United States Patent [19]

Suzuki et al.

[11] Patent Number: 4,789,588
[45] Date of Patent: Dec. 6, 1988

[54] SURFACE MATERIALS FOR ABSORPTIVE PRODUCTS

[75] Inventors: Masayasu Suzuki; Masahiko Taniguchi, both of Moriyama; Taizo Sugihara, Omihachiman, all of Japan

[73] Assignee: Chisso Corporation, Osaka, Japan

[21] Appl. No.: 79,014

[22] Filed: Jul. 29, 1987

[30] Foreign Application Priority Data

Aug. 1, 1986 [JP] Japan .............................. 61-181548
Aug. 18, 1986 [JP] Japan .............................. 61-192515

[51] Int. Cl.$^4$ .............................................. D21H 5/20
[52] U.S. Cl. .................................. 428/288; 428/289; 428/290
[58] Field of Search .................... 428/288, 289, 290

[56] References Cited

U.S. PATENT DOCUMENTS 4,655,877  4/1987  Horimoto et al. .................. 428/288
4,721,647  1/1988  Nakanishi et al. .................. 428/288

Primary Examiner—Marion C. McCamish
Attorney, Agent, or Firm—Oblon, Fisher, Spivak, McClelland & Maier

[57] ABSTRACT

A surface material for absorptive products comprising a succession of fluid permeable surface layers comprising a nonwoven fabric, an absorptive layer and a backing layer unpervious to fluid being provided, the nonwoven fabric comprising fibers of which surface of 50% or more being occupied by a hydrophobic resin, and a 0.1 to 1.0 weight % of a finishing agent being deposited onto the surface of the fibers. The finishing agent comprises a mixture of a sorbitan monooleate with a polyoxyethylene sorbitan monooleate in a weight ratio of 1:1 to 9:1. The fibers may further contain a specific wetting agent.

6 Claims, No Drawings

SURFACE MATERIALS FOR ABSORPTIVE PRODUCTS

BACKGROUND OF THE INVENTION

Field of the Invention

The present invention relates to a surface or liner material for absorptive products such as paper diapers or sanitary napkins.

Statement of the Prior Art

Absorptive products now enjoying wide use such as disposable diapers, are composed of three layers arranged in the order of a surface or liner layer, an absorbent layer and a backing layer unpervious to liquid, from the layer contacting the skin of the user's body. The linear layer is required to have, in addition to strength and softness, fluid permeability that permits fluid excrement to be absorbed to reach rapidly the absorbent layer, and a dry touch nature that prevents the fluid excrement absorbed from flowing-back to the skin and presents a dry feel to the skin. To meet such requirements, nonwoven fabrics comprising hydrophobic fibers have frequently been used, as proposed in the following three U.S. patent specifications. U.S. Pat. No. 3,695,269 discloses absorbent products comprising at least two fibrous layers; one layer comprising a highly absorbent fibrous mass having excellent absorption and retention capacity for body fluids and exudates; and a second layer comprising a relatively dry, non-adherent, non-woven fabric facing made of relatively non-absorbent, hydrophobic, synthetic fibres bonded with a hydrophobic binder material and processed so as to be provided with increased loft and bulk properties. U.S. Pat. No. 4,041,951 teaches that a topsheet of the absorptive device, such as disposable diapers, presenting a dry feel to the user is preferably constructed from a moisture-pervious, generally hydrophobic, nonwoven fibrous web. U.S. Pat. No. 4,391,869 states that fibers suitable for use in the invention are resilient, synthetic, staple fibers which generally are hydrophobic. However, use of nonwoven fabrics having such strong hydrophobic nature has resulted in improvements in the dry touch nature, but led to a lowering in fluid permeability. To make use of both dry touch nature and fluid permeability in a well-balanced state, attempts have therefore been made to apply a finish comprising usual surfactants on the surface of hydrophobic fibers.

In recent years, diverse requirements have been imposed upon absorptive products. For absorptive products designed to be used at night in particular, it is required to retain suitable degrees of fluid permeability and dry touch nature ever after a repeated excretion and absorption of fluid excrement several times. In view of such a requirement, the liner materials formed of nonwoven fabrics comprising hydrophobic fibers having a conventional surface active agent deposited thereon have the disadvantage that, upon absorbing fluid excrement once or twice, that agent flows away, thus resulting in a sharp drop in fluid permeability.

SUMMARY OF THE INVENTION

It is therefore an object of the present invention to eliminate the disadvantages of the conventional surface or liner materials and provide a surface or liner material (hereinafter referred to as the surface material or materials) for absorptive products, which can retain suitable degrees of fluid permeability and dry touch nature even after subjected to repeated absorption of fluid excrement.

According to one specific aspect of the present invention, there is provided a surface material for absorptive products, which is composed of a nonwoven fabric comprising fibers of which surface of 50% or more are occupied by a hydrophobic resin; said fibers having a finishing agent deposited on the surface thereof in an amount of 0.1 to 1.0 weight %, which finishing agent consists of a mixture of a sorbitan monooleate and polyoxyethylene sorbitan monooleate in a weight ratio range of 1:1 to 9:1.

According to another specific aspect of the present invention, a more improved surface material for absorptive products having above-mentioned specific aspect are obtained by adding 0.05 to 10.0 weight % of a wetting agent to the aforesaid nonwoven fabric comprising fibers of which surface of 50% or more are occupied by a hydrophobic resin.

PREFERRED EMBODIMENTS OF THE INVENTION

The term "hydrophobic resin" used in the present disclosure refers to a resin having a equilibrium mositure content of 0.5% or lower, and is specifically exemplified by a variety of polyethylene, polypropylene, polyester and ethylene-vinyl acetate copolymers. Such hydrophobic resins may be used alone or in admixture.

With the surface material comprising fibers of which surface of 50% or more are occupied by such a hydrophobic resin (hereinafter simply called said fibers the main-surface-hydrophobic-fibers), it is possible to reduce flowing-back of fluid excrement from the absorptive layer and give a dry touch nature to the associated absorptive product, even where it absorbs fluid excrement.

Without any wetting agent, the hydrophobic resin may be used to form the nonwoven fabric forming fibers. In order to give an appropriate degree of hydrophilic nature to the end surface materials, however, it should preferably be used with the addition of a suitable amount of the wetting agent to be defined later.

For such a wetting agent, the following agents have been selected in view of the thremal stability at the time of spinning, the capability of giving a hydrophilic nature to the hydrophobic resin and the like. That is to say, use should be made of one or more compounds selected from the group consisting of a fatty acid monoglyceride and a fatty acid diglyceride expressed by General Formula I:

$$CH_2(OR_1)CH(OR_2)C_2(OR_3) \qquad I$$

where $OR_1$, $OR_2$ and $OR_3$ independently represent a hydroxy group or a saturated or unsaturated fatty acid ester group having 12 to 18 carbon atoms, and one or two of $OR_1$, $OR_2$ and $OR_3$ is said ester group (a saturated or unsaturated fatty acid ester group is also expressed as "alkanoyloxy group or alkenoyloxy group"), or a polyoxyethylene glycol fatty acid monoester expressed by General Formula II:

$$HOCH_2CH_2(OCH_2CH_2)nOR_4 \qquad II$$

where $OR_4$ is a saturated or unsaturated fatty acid ester group having 12 to 18 carbon atoms, and n is an integer between 10 and 55. Further, admixtures of at least two compounds selected from said compound groups may be used as a wetting agent.

Incorporation of the wetting agent to the hydrophobic resin may be achieved by usual heating and kneading. For more convenience, an extruder may be used at the time of spinning. The wetting agent should preferably be added to the hydrophobic resin in an amount of 0.05 to 10.0 weight %. This is because in the addition in an amount below 0.05 weight %, the wetting agent is less effective in affording the hydrophilic nature, and in the addition in an amount exceeding 10.0 weight %, it gives rise lowering of spinnability or lowering in the dry touch nature of the surface material.

The hydrophobic resin with or without the wetting agent forms independently usual fibers, or is made composite with other resin to form composite fibers of two types of composite structure, side-by-side and sheath-core. In the latter case of forming composite fibers, the resin to be made composite with the hydrophobic resin may include a hydrophilic resin such as polyamide in addition to a hydrophobic resin. In order to obtain the composite fibers of which surface of 50% or more are occupied by the hydrophobic resin, said resin may be located on the sheath layer for the sheath-core type of which surface is occupied completely by sheath component. Alternatively, for the side-by-side type, the composite fibers may be obtained by a suitable composite ratio (i.e, a weight ratio of composite components), since the fiber surface structure (the surface ratio of each component) varies mainly with that composite ratio, and the suitable composite ratio which varies with the kinds and combinations of composite components may be obtained by trial and error. Preferably, the composite fibers having above-mentioned structure are of the side-by-side or sheath-core type composed of two kinds of components with the difference of 20° C. or more in melting points wherein 50% or more of the fiber surface are occupied by the lower-melting point component. This is because, in such a case, a thin but strong nonwoven fabric can easily be obtained by heat treatment with a suction dryer, a heated roller and the like at a temperature between the melting points of both components. In the simplest structure of such composite fibers, the lower-melting point component consists of the hydrophobic resin, while the higher-melting point component may be a resin of either hydrophobic or hydrophilic nature.

The surface materials according to the present invention are a nonwoven fabric comprising such main-surface-hydrophobic-fibers. The nonwoven fabric may be obtained by the aforesaid heat treatment or suitable known techniques using needle punch, water needle or the like.

The sorbitan monooleate and polyoxyethylene sorbitan monooleate used as components of finishing agent in the present invention are represented by the following General Formulae III and IV respectively:

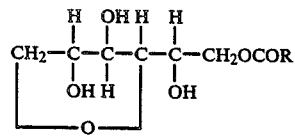

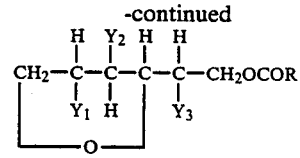

where R is $C_{17}H_{33}$, and in General Formulae IV, $Y_1$, $Y_2$ and $Y_3$ each independently are a hydroxyl group or $-O(CH_2CH_2O)mH$, provided that at least one of $Y_1$, $Y_2$ and $Y_3$ is $-O(CH_2CH_2O)mH$, and m is an integer between 10 and 55, thus polyoxyethylene sorbitan monooleale is admixtures of various sorbitan monoesters.

The finishing agent comprising the sorbitan monooleate and the polyoxyethylene sorbitan monooleate in a weight ratio of 1:1 to 9:1, preferably 1:1 to 3:1 is deposited onto the fibers forming the nonwoven fabric in an amount of 0.1 to 1.0 weight %. This is because in addition in an amount of below 0.1 weight %, the achieved fluid permeability is insufficient, and in addition in an amount exceeding 1.0 weight %, the achieved dry touch nature is insufficient. Deposition of said finishing agent onto the fibers forming the nonwoven fabric may be achieved by any one of the techniques known in the art, e.g., by using an oiling roll during spinning, or impregnating the completed nonwoven fabric in it.

EXAMPLES AND COMPARATIVE TESTS

The present invention will now further be explained with reference to two groups of examples/comparative tests given for the purpose of illustration alone. Various fibers used therein were prepared in the following manner.

In the first group (Ex. 1 to 6 & Comp. T. 1 to 8), hydrophobic resins of polyethylene, polypropylene and polyester and a hydrophilic resin of 6-nylon were used as the fibrous components without any modification made thereto. In the second group (Ex. 7 to 10 & Comp. T. 9 to 15), the same hydrophobic resins (except for polyester) as in the first group were kneaded uniformly with the wetting agents in spinning process by making said wetting agents be supplied to a spinning extruder, and the resulted products were used as the whole or a part of the fiber-composing components. In both the first and second groups, various long fibers of the predetermined structure in cross-section were prepared by means of the known techniques, then mechanically crimped, and thereafter cut to a length of 56 mm into staple fibers.

These staple fibers were formed into webs with a 40-inch roller card, and the webs were in turn formed into nonwoven fabrics by means of various methods to be shown later. The finishing agent to be shown later was deposited onto each fibers before forming nonwoven fabric by an oiling roll during spinning when the method of making nonwoven fabric is one using a suction dryer or a heated roller. Alternatively, when the nonwoven fabric was obtained with the use of a water needle, such deposition was effected by impregnation.

Estimation of the thus obtained nonwoven fabrics in terms of the surface materials were based on water permeability after repeated water permeation (hereinafter referred to as the repetitive water permeability) and dry touch nature. The testing procedures are given below:

Testing Procedure for Repetitive Water Permeation

A test piece of 20 cm×20 cm is placed on filter paper of the same size, and 1 ml of water is added dropwise to the central portion of the test piece in five seconds from the tip of a burette located at a height of 1 cm from the surface thereof. After the completion of the dropwise addition, measurement is made of a duration of (water permeation) time at the end of which the reflection of light from the test piece's surface due to water droplets disappears. Then, this test piece is dried at 40° C. for one hour, after which the water permeation time is again measured. This operation is repated until the water permeation time reaches three seconds to determine the number of repetition.

Testing Procedure for Dry Touch Nature

A test piece of 20 cm×20 cm is placed on filter paper of the same size, and 1 ml of water is added dropwise to the central portion of the test piece in five seconds. After one minute, the water-added portions of the test piece are lightly pressed by hand to determine the presence of a wetting feel. The presence and absence of a wetting feel are designated as × and O, respectively.

Various abbreviations in the tables to be given later represent the following materials.
PP: polypropylene
PE: polyethylene
PET: polyester
A: sorbitan monooleate
B: polyoxyethylene sorbitan monooleate (with the degree of polymerization being 20)
C: lauryl phosphate K salt+sorbitan tallow fatty acid ester (1+1 admixture)
D: K salt of lauryl phosphate+polyoxyethylene laurate (1+1 admixture, the degree of polymerization being 9)
E: K salt of octyl phosphate+K salt of lauryl phosphate (1+1 admixture)
d/f: deniers per filament

EXAMPLES 1 TO 6 & COMPARATIVE TESTS 1 TO 8

Table 1 shows the cross-sectional structure types, components, fiber surface structure (the surface ratio of each component, hereinafter referred to as surface component ratio) and degree of fineness of various fibers forming the nonwoven fabrics; the preparatory methods and weight per square meter of the nonwoven fabrics as well as the finishing agent types; and the components (component ratios), amounts of deposition and methods for deposition of the finishing agent. In the column "Method for Deposition", the term "fiber" indicates the method by using an oiling roll, and the term "nonwoven fabric" the method by impregnation. Table 1 also shows the results of estimation of the various nonwoven fabrics obtained in terms of the surface materials.

TABLE 1

| | Fiber | | | | Finishing Agent | | | | |
|---|---|---|---|---|---|---|---|---|---|
| | Component (Surface Component Ratio) | Cross-Sectional Structure Type | Fineness (d/f) | Method for Preparation of Nonwoven Fabric | Weight (g/m$^2$) | Component (Component Ratio) | Amount of Deposition (wt %) | Method for Deposition | Repetitive Water Permeability | Dry Touch Nature |
| Example 1 | PP/PE (40/60) | Side-by-Side | 3 | Suction Dryer | 20 | A/B (75/25) | 0.3 | Fiber | 5 | O |
| Example 2 | PP/PE (0/100) | Sheath-Core | 3 | Suction Dryer | 22 | A/B (75/25) | 0.9 | Fiber | 5 | O |
| Example 3 | PP | Single | 2 | Water Needle | 18 | A/B (50/50) | 0.5 | Nonwoven Fabric | 5 | O |
| Example 4 | PE | Single | 3 | Heated Roll | 20 | A/B (80/20) | 0.4 | Fiber | 5 | O |
| Example 5 | 6-Nylon/ PP (20/80) | Side-by-Side | 3 | Heated Roll | 22 | A/B (75/25) | 0.3 | Fiber | 5 | O |
| Example 6 | PET/PE (0/100) | Sheath-Core | 3 | Suction Dryer | 23 | A/B (60/40) | 0.2 | Fiber | 4 | O |
| Comparative Test 1 | PP | Single | 3 | Water Needle | 20 | A/B (50/50) | 0.05 | Nonwoven Fabric | 1 | O |
| Comparative Test 2 | PP/PE (40/60) | Side-by-Side | 3 | Suction Dryer | 18 | A/B (75/25) | 1.4 | Fiber | 5 | X |
| Comparative Test 3 | 6-Nylon/ PP (60/40) | Side-by-Side | 3 | Heated Roll | 23 | A/B (75/25) | 0.5 | Fiber | 5 | X |
| Comparative Test 4 | PP/PE (40/60) | Side-by-Side | 3 | Suction Dryer | 20 | A/B (95/5) | 0.4 | Fiber | 1 | O |
| Comparative Test 5 | PP/PE (40/60) | Side-by-Side | 3 | Suction Dryer | 21 | A/B (40/60) | 0.4 | Fiber | 1 | O |
| Comparative Test 6 | PP/PE (40/60) | Side-by-Side | 3 | Suction Dryer | 20 | C (100) | 0.3 | Fiber | 1 | O |
| Comparative Test 7 | PP/PE (40/60) | Side-by-Side | 3 | Suction Dryer | 20 | D (100) | 0.3 | Fiber | 1 | O |
| Comparative Test 8 | PP/PE (40/60) | Side-by-Side | 3 | Suction Dryer | 25 | E (100) | 0.3 | Fiber | 1 | O |

From Table 1, it is found that the surface materials according to the present invention are superior in the repetitive water permeability and dry touch nature, but those according to the comparative tests are inferior in either one of the two properties. It is noted that the following subjects of each comparative test are out of the scope of the present invention respectively; the amounts of deposition of the finishing agent in Comparative Tests 1 and 2; the surface component ratio of the hydrophobic fibers in Comparative Test 3; the component ratios of the finishing agent in Comparative Tests 4 and 5; and the components per se of the finishing agent in Comparative Tests 6 to 8.

EXAMPLES 7 TO 10
COMPARATIVE TESTS 9 TO 15

In the instant examples and comparative tests, the hydrophobic resin components forming the nonwoven fabrics are added with, and contain, the wetting agents. To avoid too large tabulation, the details of the fibers are separately shown in Table 2, and the remaining materials and properties are indicated in Table 3.

TABLE 2

| | Component (Surface Component Ratio) | Cross-Sectional Structure Type | Wetting Agent | Content (wt %) | Fineness (d/f) |
|---|---|---|---|---|---|
| Fiber | | | | | |
| a | PP/PE (40/60) | Side-by-Side | Stearic Acid Monoglyceride | PE side, 5 | 3 |
| b | PP/PE (0/100) | Sheath-Core | Polyoxyethylene Glycol Mono Oleate | PE side, 2 | 6 |
| c | PP | Single | Stearic Acid Monoglyceride | 3 | 2 |
| d | 6-Nylon/PP (40/60) | Side-by-Side | Stearic Acid Monoglyceride | PP side, 0.1 | 6 |
| e | 6-Nylon/PP (60/40) | Side-by-Side | Stearic Acid Monoglyceride | PP side, 0.1 | 6 |

TABLE 3

| | Fiber | Method for Preparation of Nonwoven Fabric | Weight (g/m²) | Finishing Agent Component (Component Ratio) | Amount of Deposition (wt %) | Method for Deposition | Repetitive Water Permeability | Dry Touch Nature |
|---|---|---|---|---|---|---|---|---|
| Example 7 | a | Suction Dryer | 20 | A/B (75/25) | 0.3 | Fiber | 7 | O |
| Comparative Test 9 | a | Suction Dryer | 20 | A/B (50/50) | 0.05 | Fiber | 1 | O |
| Comparative Test 10 | a | Suction Dryer | 22 | A/B (75/25) | 1.5 | Fiber | 8 | X |
| Comparative Test 11 | a | Suction Dryer | 23 | A/B (40/60) | 0.4 | Fiber | 1 | O |
| Comparative Test 12 | a | Suction Dryer | 19 | A/B (95/5) | 0.4 | Fiber | 1 | O |
| Example 8 | b | Suction Dryer | 21 | A/B (60/40) | 0.2 | Fiber | 7 | O |
| Example 9 | c | Water Needle | 20 | A/B (70/30) | 0.4 | Nonwoven Fabric | 7 | O |
| Comparative Test 13 | c | Water Needle | 22 | C | 0.3 | Nonwoven Fabric | 1 | O |
| Comparative Test 14 | c | Water Needle | 23 | D | 0.3 | Nonwoven Fabric | 1 | O |
| Example 10 | d | Heated Roll | 24 | A/B (75/25) | 0.5 | Fiber | 7 | O |
| Comparative Test 15 | e | Heated Roll | 24 | A/B (75/25) | 0.5 | Fiber | 7 | X |

From Tables 2 and 3, it is found that the examples 7 to 10 of the present invention provide surface materials considerably improved by allowing the wetting agents to be contained in the hydrophobic resin components which occupy 50% or more of the surface of the fibers foming the surface materials. However, it is noted that the surface materials, in which the wetting agents are contained, but do not meet the requirements as defined in the present disclosure, are inferior. In other words, the surface materials according to the comparative tests are found to be inferior in either one of the repetitive water permeability and dry touch nature, as can be understood from Comparative Tests 9 and 10 in which the amounts of deposition of the finishing agent depart from the presently defined scope; Comparative Tests 11 and 12 in which the component ratios of the finishing agent do, Comparative Tests 13 and 14 in which the components per se of the finishing agent do; and Comparative Test 15 in which the surface component ratio of the hydrophobic resin does.

From the results of Tables 1 and 3, it is clearly understood that the surface materials of the present invention excel in the repetitive water or fluid permeability and dry touch nature, and are so suitable for use with disposable night diapers required to repeatedly absorb fluid excrement such as urine.

What is claimed is:

1. A surface material for absorptive products comprising a succession of fluid permeable surface layers comprising a nonwoven fabric, an absorptive layer and a backing layer unpervious to fluid, wherein said nonwoven fabric is a nonwoven fabric comprising fibers of which surface of 50% or more are occupied by a hydrophobic resin, and a 0.1 to 1.0 weight % of a finishing agent is deposited onto the surface of said fibers, said finishing agent comprising a mixture of a sorbitan monooleate with a polyoxyethylene sorbitan monooleate in a weight ratio of 1:1 to 9:1.

2. A surface material as defined in claim 1, wherein said fibers of which surface of 50% or more are occupied by a hydrophobic resin contain 0.05 to 10.0 weight % of wetting agents comprising one or more compounds selected from the group consisting of a fatty acid monoglyceride, a fatty acid diglyceride and a polyoxyethylene glycol fatty acid monoester.

3. A surface material as defined in claim 1 or 2, wherein said hydrophobic resin is polyethylene.

4. A surface material as defined in claim 1 or 2, wherein said hydrophobic resin is polypropylene.

5. A surface material as defined in claim 1 or 2, wherein said hydrophobic resin is polyester.

6. A surface material as defined in claim 1 or 2, wherein said fibers of which surface of 50% or more are occupied by a hydrophobic resin are either composite fibers of the sheath-core type or side-by-side type composed of two components with the difference of 20° C. or more in melting points wherein 50% or more of the surface of said fibers are occupied by the lower-melting point component.

* * * * *